United States Patent [19]
Takai et al.

[11] Patent Number: 6,015,936
[45] Date of Patent: Jan. 18, 2000

[54] BODY FLUIDS ABSORBENT ARTICLE

[75] Inventors: Hisashi Takai; Hiroki Goda; Tomoko Tsuji, all of Kagawa, Japan

[73] Assignee: Uni-Charm Corporation, Ehime-ken, Japan

[21] Appl. No.: 09/128,449

[22] Filed: Aug. 3, 1998

[30] Foreign Application Priority Data

Sep. 4, 1997 [JP] Japan ..................................... 9-239610

[51] Int. Cl.$^7$ ..................................................... A61F 13/15
[52] U.S. Cl. ........................ 604/383; 604/358; 604/365; 604/366; 604/367; 604/370; 604/378; 604/385.1; 604/385.2
[58] Field of Search .................................... 604/369, 384, 604/385.1, 383, 358, 365, 366, 367, 370, 378, 385.2; 428/163

[56] References Cited

U.S. PATENT DOCUMENTS

| | | |
|---|---|---|
| H1377 | 11/1994 | Perry ..................................... 604/385.1 |
| 3,559,648 | 2/1971 | Mason ..................................... 128/287 |
| 5,268,213 | 12/1993 | Murakami et al. ..................... 428/163 |
| 5,387,209 | 2/1995 | Yamamoto et al. .................... 604/384 |
| 5,827,253 | 10/1998 | Young et al. ........................... 604/369 |

FOREIGN PATENT DOCUMENTS

| | | |
|---|---|---|
| 0 792 629 | 9/1997 | European Pat. Off. . |
| 9-48057 | 2/1997 | Japan . |
| 2 310 606 | 9/1997 | United Kingdom . |

*Primary Examiner*—John G. Weiss
*Assistant Examiner*—Miley C. Peppers, III
*Attorney, Agent, or Firm*—Barnes & Thornburg

[57] ABSTRACT

A body fluids absorbent article has a liquid-permeable topsheet formed by a nonwoven fabric of thermoplastic synthetic fibers. The topsheet is formed with a plurality of openings each having a diameter of 0.5~3 mm. These openings queue up so as to form plural columns of openings extending in parallel one to another. One half or more of a total number of the openings are reinforced by strands of thermoplastic synthetic resin each having a diameter of 0.1~0.5 mm and extending circumferentially of the respective openings.

15 Claims, 3 Drawing Sheets

6,015,936

BODY FLUIDS ABSORBENT ARTICLE

BACKGROUND OF THE INVENTION

This invention relates to body fluids absorbent articles such as sanitary napkins and disposable diapers comprising a liquid-absorbent core and a liquid-permeable topsheet covering the core.

Japanese Laid-Open Patent Application No. Hei9-48057 discloses an absorbent article comprising a topsheet made of plastic film formed with a plurality of liquid-permeable openings and strands each having a diameter smaller than a diameter of the opening, wherein the strands extend across the openings and are heat-sealed with the topsheet. With the topsheet, the strands contribute to avoid undesirable deformation of the openings as well as clogging thereof due to the deformation and to maintain a desired liquid-permeability of the topsheet.

According to the arrangement of the well known topsheet, each opening is divided by the associated strand at least in two. If the strand extends across the opening so as to be unacceptably one-sided with respect to a center of this opening, one of the strand-divided two sections will have an area that is insufficient to function as a liquid-permeable opening-section.

SUMMARY OF THE INVENTION

In view of the problem described above, it is a an object of the invention to provide a body fluids absorbent article including a topsheet adapted to avoid deformation as well as clogging of liquid-permeable openings thereof without deterioration of its liquid-permeability.

The object set forth above is achieved, according to the invention, by a body fluids absorbent article having a liquid-absorbent core at least partially covered with a liquid-permeable topsheet, wherein: the topsheet is formed by a nonwoven fabric made from thermoplastic synthetic fibers with a fineness of 0.05~8 deniers so as to have a basis weight of 10~50 g/m$^2$; the topsheet is defined by a skin-contactable surface intended to come in contact with the wearer's skin and a skin-noncontactable surface intended not to come in contact with the wearer's skin; a plurality of openings each having a diameter of 0.5~3 mm extend through from the skin-contactable surface to the skin-noncontactable surface of the topsheet, on one hand, and queue up in parallel one to another so as to form a plural columns of the openings, on the other hand; and, in one half or more of a total number of the openings, strands of thermoplastic synthetic resin each having a diameter of 0.1~0.5 mm extend along and are bonded to circumferential parts of peripheral edges of the openings defined at the level of the skin-contactable surface and/or peripheral walls of the respective openings extending between the skin-contactable and skin-noncontactable surfaces.

Preferably, the topsheet includes tubular portions extending downward from the peripheral edges of the respective openings defined at the level of the skin-contactable surface and portions of the strands extend along and are bonded to circumferential parts of inner peripheral surfaces of the respective tubular portions.

Preferably, the strands extend in parallel to the columns of openings and are bonded to the skin-contactable surface of the topsheet between each pair of adjacent openings in each column of openings.

Preferably, the strands and the nonwoven fabric are bonded together by means of heat-sealing.

DESCRIPTION OF THE PREFERRED EMBODIMENTS

Details of a body fluids absorbent article according to the invention will be more fully understood from the description given hereunder with reference to the accompanying drawings.

Figure 1:
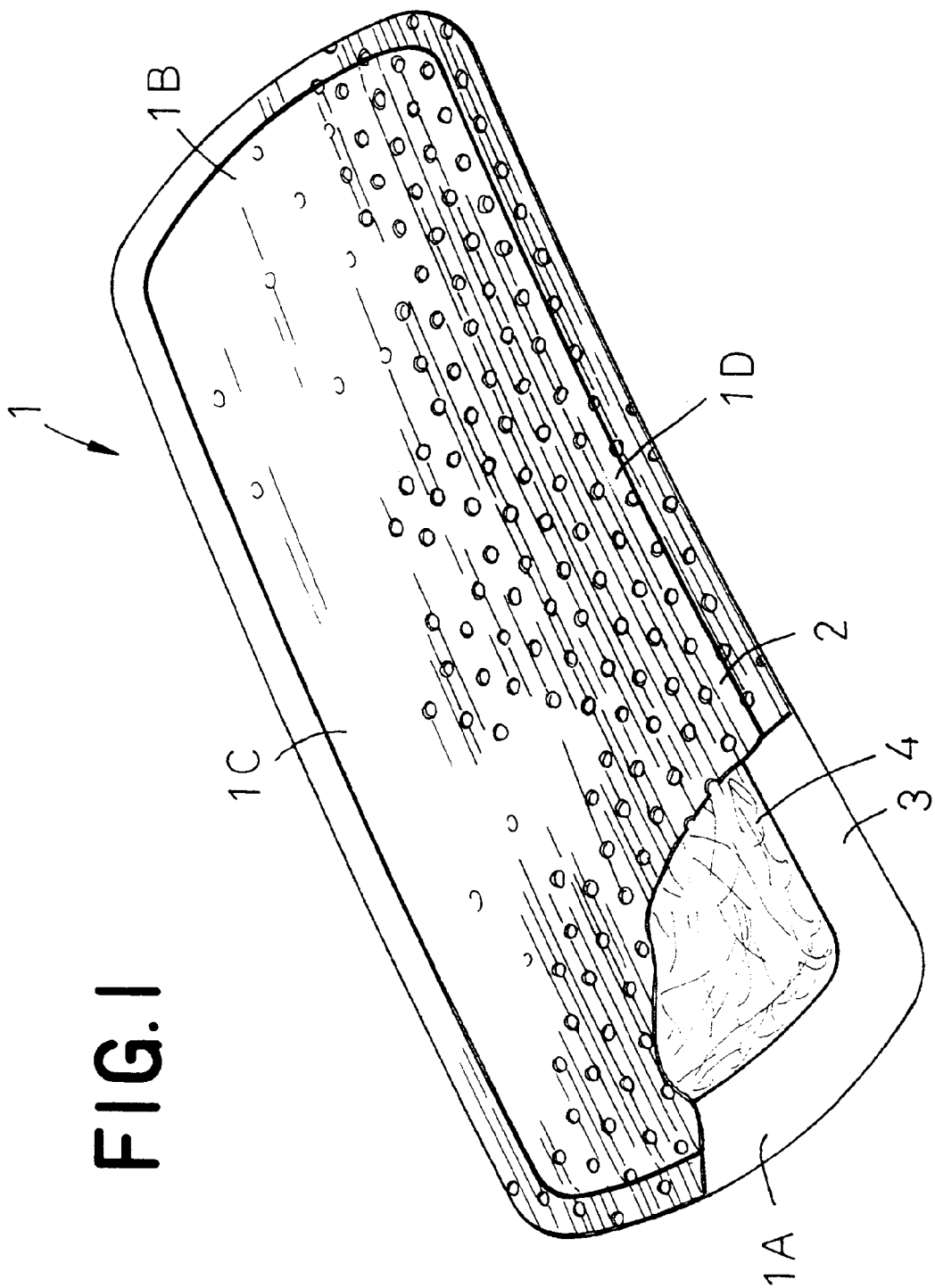
FIG. 1 is a perspective view showing a sanitary napkin according to the invention as partially broken away.

A sanitary napkin 1 shown by FIG. 1 in a perspective view as partially broken away is a specific embodiment of a body fluids absorbent article. The napkin 1 is defined by longitudinally opposite ends 1A, 1B and transversely opposite side edges 1C, 1D extending between the opposite ends 1A, 1B. The napkin 1 includes a liquid-permeable topsheet 2, a liquid-impermeable backsheet 3 and a liquid-absorbent core 4 disposed between these two sheets 2, 3. The topsheet 2 covers the absorbent core 4 at least on its skin-contactable side. The topsheet 2 and the backsheet 3 extend outward beyond a peripheral edges of the absorbent core 4 and are put flat and bonded together along the respective extensions. The absorbent core 4 is preferably bonded to an inner surface of the topsheet 2 or the backsheet 3 by means of hot melt adhesive (not shown) intermittently applied thereon.

Figure 2:
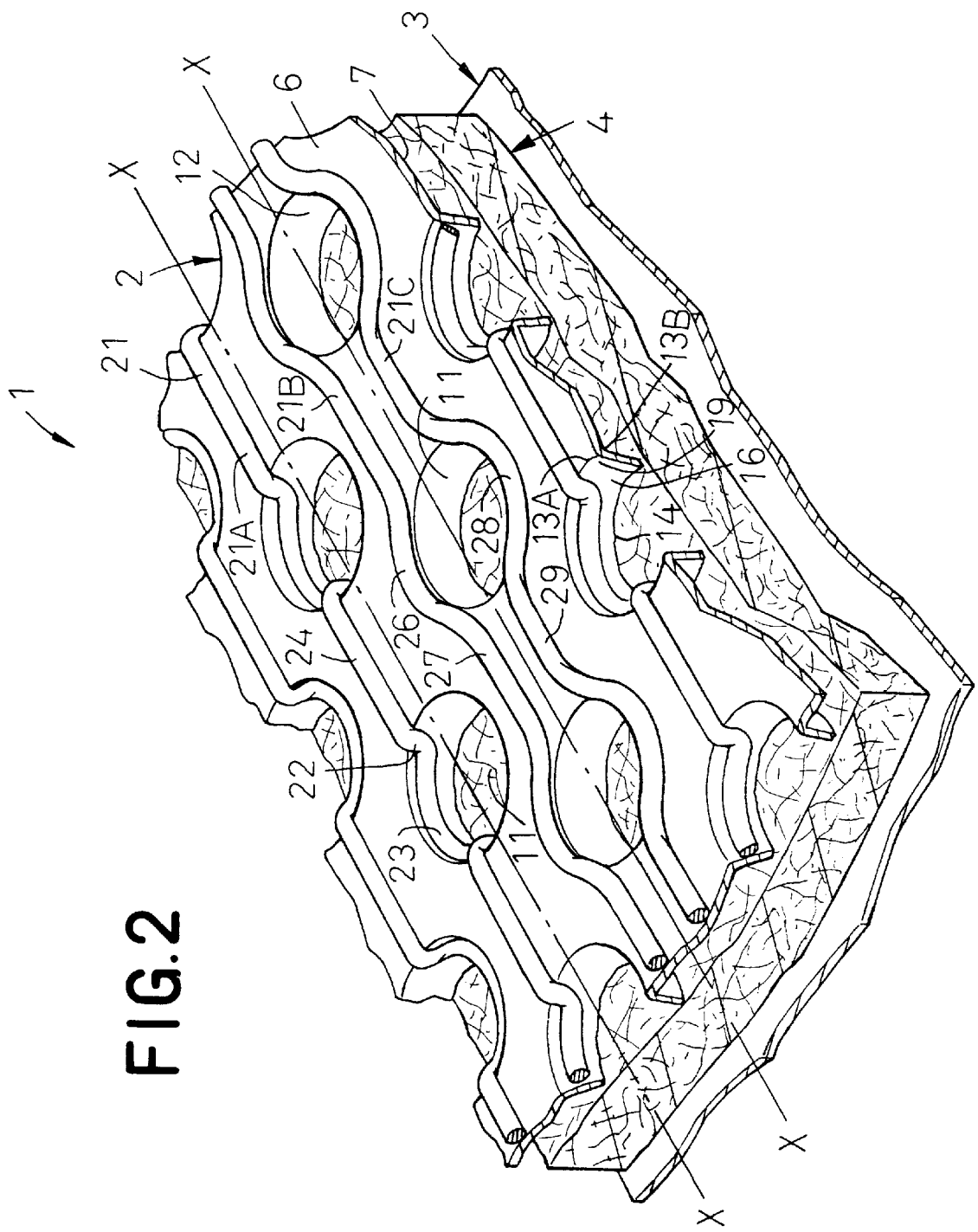
FIG. 2 is a fragmentary perspective view showing a portion of FIG. 1 in an enlarged scale.

FIG. 2 is a fragmentary perspective view showing a portion of the napkin in an enlarged scale. The topsheet 2 is formed by a nonwoven fabric made of thermoplastic synthetic fibers with a fineness of 0.05~8 deniers so as to have a basis weight of 10~50 g/m$^2$. The topsheet 2 has a skin-contactable surface 6 and a skin-noncontactable surface 7. The topsheet 2 is formed with a plurality of liquid-permeable openings 11 each having a diameter of 0.5~3 mm. These openings 11 queue up along imaginary lines X—X, respectively, to form columns of the openings extending in parallel one to another longitudinally of the napkin 1. In each column of the openings 11, each pair of adjacent openings 11 are spaced apart from each other by a center-to-center distance of 1~7 mm. Each of these openings 11 has an upper peripheral edge 13A at the level of the skin-contactable surface 6 and a tubular portion 12 extending downward from a lower peripheral edge 13B at the level of the skin-noncontactable surface 7. Each of the openings 11 is defined by a peripheral surface 19 extending between the skin-contactable surface 6 and the skin-noncontactable surface 7 and an inner peripheral surface 16 of the tubular portion 12. A lower end 14 of the tubular portion 12 is in contact with the liquid-absorbent core 4.

On the skin-contactable surface 6 of the topsheet 2, a plurality of thermoplastic synthetic resin strands 21 extend in parallel to the columns of the openings 11 longitudinally of the napkin 1. Of the strands 21 shown in FIG. 2, the strand 21A comprises relatively short segments 22 each extending downward along the peripheral surfaces 19 of the respective openings 11, segments 23 extending circumferentially of the peripheral surface 19 or the inner peripheral surface 16 along up to ½ of circumferences of the respective openings 11 and segments 24 each longitudinally extending between each pair of adjacent openings 11 in this column. The strand 21B includes segments 26 each extending along parts of the upper peripheral edges 13A of the respective openings 11 and segments 27 each extending between each pair of adjacent openings 11 in this column. The strand 21C is opposed to the strand 21B with the openings 11 therebetween and comprises, similarly to the strand 21B, segments 28 each extending along parts of the upper peripheral edges 13A and segments 29 each extending between each pair of adjacent openings 11 in this column. The segments 26, 28 may have their lengths up to ½ of the circumference of the opening 11, respectively.

The nonwoven fabric and the strands forming together the topsheet 2 are bonded together by heat-sealing at least one of the nonwoven fabric and the strands 21. Of these strands 21, the strand 21A circumferentially extends along the inner peripheral surfaces 16 of the respective tubular portions 12 and thereby prevents the tubular portions 12 from being radially deformed. Both the strand 21B and the strand 21C extend along the upper peripheral edges 13A of the respective tubular portions 12 and thereby prevent the upper peripheral edges 13A from being deformed. The segments 23, 26, 28 of the respective strands 21A, 21B, 21C extending circumferentially of the openings 11 may have their lengths up to ½ of the circumferences of respective openings 11. Particularly when a column of the openings 11 is reinforced by a pair of adjacent strands, for example, the strands 21B, 21C, each opening 11 is reinforced thereby along ½ or more of its circumference or along its substantially entire circumference.

According to a specific embodiment, the topsheet 2 may be formed by a point bonded nonwoven fabric made of polypropylene/polyethylene conjugated fibers having a fineness of 4 deniers, a fiber length of 51 mm and a basis weight of 20 g/m². The strands 21 may be obtained, for example, by extrusion-molding a mixture of 80% by weight of ultra low density polyethylene having a MI (melt index) =20 and a density of 0.905, 15% by weight of micro crystalline wax and 5% by weight of coloring agent.

While the topsheet 2 is preferably formed by a hydrophobic nonwoven fabric, this hydrophobic nonwoven fabric may be partially, for example, in the proximity of the lower ends 14 of the respective tubular portions 12, treated so as to become hydrophilic or the hydrophobic nonwoven fabric may be replaced by a hydrophilic nonwoven fabric.

The backsheet 3 may be formed by a plastic film or a laminate of plastic film and nonwoven fabric.

The absorbent core 4 may be formed by fluff pulp or a mixture of fluff pulp and polymer of high water absorptivity. It is also possible to cover the mixture with tissue paper.

With the sanitary napkin 1 constructed as described hereinabove, the openings 11 are well protected against undesirable deformation and clogging even if the wearer's body weight is exerted on the topsheet 2 of the napkin 1 put on the wearer's body.

Figure 3:
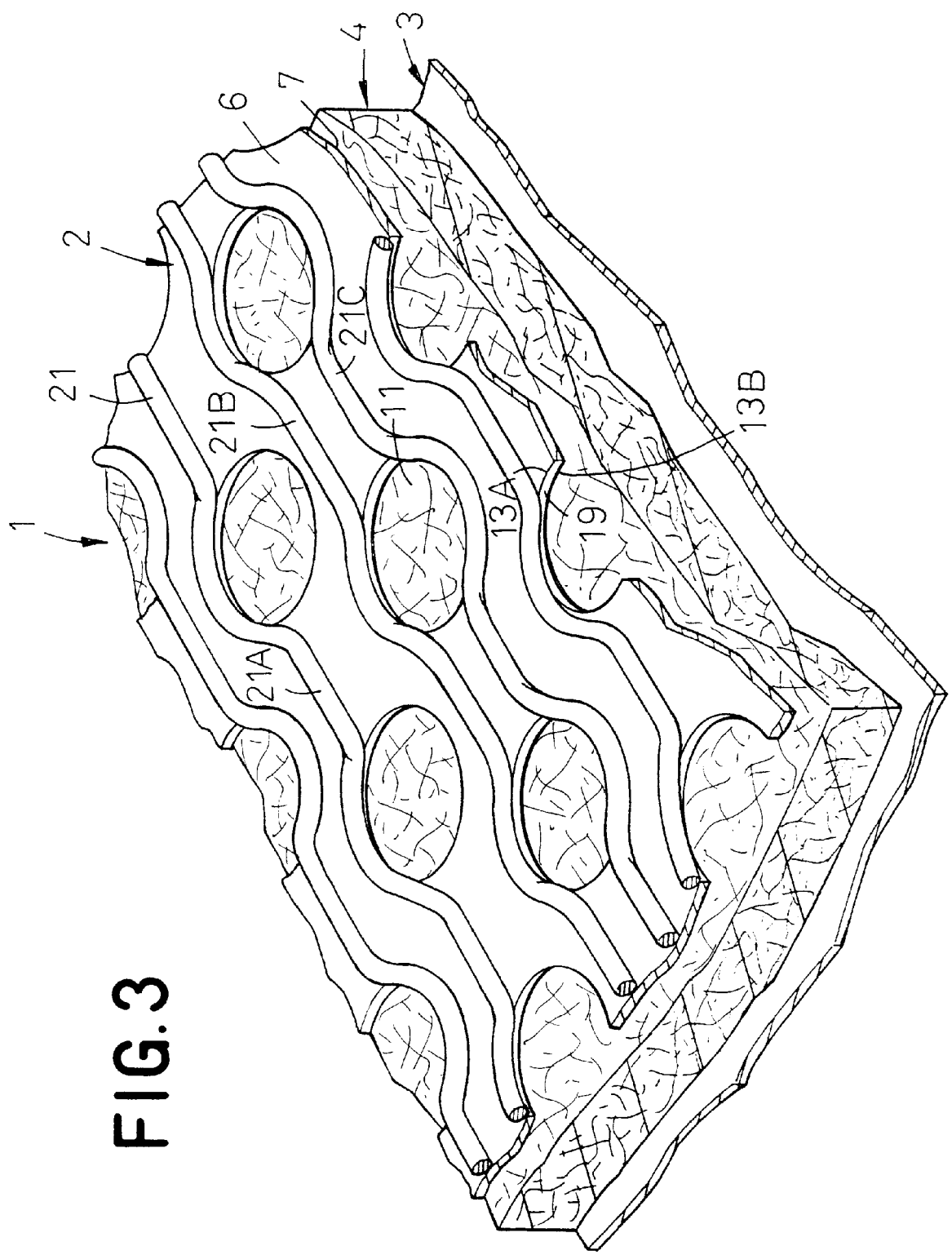
FIG. 3 is a view similar to FIG. 2 showing an alternative embodiment of the invention.

FIG. 3 is a view similar to FIG. 2 showing an alternative embodiment of the invention. Also in this embodiment of the napkin 1, the openings 11 extend through the topsheet 2 from the skin-contactable surface 6 to the skin-noncontactable surface 7 and queue up similarly to the case of FIG. 2, the openings 11 have none of the tubular portions 12 extending downward from the skin-noncontactable surface 7. The strands 21 circumferentially extend along parts of the upper peripheral edges 13A and/or the peripheral surfaces 19 of the respective openings 11 so as to protect the openings 11 against undesirable deformation and clogging. Similarly to the case of FIG. 2, some columns of the openings 11 are reinforced by a single strand 21A and the other columns of the openings 11 are reinforced by a pair of the strands 21B, 21C.

While the openings 11 are illustrated in FIGS. 2 and 3 as being of circular shape, they may be of polygonal, oval or indeterminate shape. The strands 21 illustrated as having a circular cross-section may be also replaced by those having polygonal, oval or indeterminate shape. In description of the invention, expression "the diameter of the opening 11" and "the diameter of the strand 21" should be understood to be the maximum diameters of the opening 11 and the strand 21, respectively.

While the strands 21 serving to reinforce the openings 11 are illustrated as continuously extending between the longitudinally opposite ends 1A, 1B of the napkin 1, these strands 21 may also be longitudinally discontinuous and, more specifically, may be intermittently laid along the respective openings and in the proximity thereof. It is not essential for the invention to reinforce all the openings 11 of the topsheet 2 by the strands 21. Depending on number and size of the openings 11, the object of the invention can be adequately achieved when one half or more of a total number of the openings 11 are reinforced by the strands 21.

The body fluids absorbent article according to the invention can be implemented, in addition to the sanitary napkin as described hereinabove in reference with the accompanying drawings, in the other various forms, for example, in the form of a disposable diaper, pants for incontinent patient or a sanitary pad.

With the body fluids absorbent article according to the invention, the openings of the topsheet are reinforced by the strands of relatively large diameter and, in consequence, there is no apprehension that the respective openings might be divided by the reinforcing strands into unacceptably small sections as the prior art has been the case.

By reinforcing each opening by a pair of strands, it is possible to reinforce substantially the entire circumference of this opening.

By circumferentially laying the strands along the inner peripheral surfaces of the respective tubular portions extending downward from the respective openings, it is possible to avoid undesirable deformation of the tubular portions which otherwise would readily occur and result in clogging.

What is claimed is:

1. A body fluids absorbent article which comprises:
   a liquid-permeable top sheet having:
      a skin-contactable surface which contacts the skin of a wearer of the article;
      a skin-noncontactable surface which does not contact the skin of a wearer of the article; and
      a plurality of openings that extend between the skin-contactable surface and the skin-noncontactable surface which openings are aligned in a two-dimensional array;
   a liquid-impermeable backsheet;
   a liquid-absorbent core positioned between the liquid-permeable topsheet and the liquid-impermeable backsheet; and
   a plurality of deformation preventing strands which extent along and are bonded to circumferential portions of a number of the plurality of the openings and thereby prevent deformation of the openings.

2. The article according to claim 1, wherein a pair of deformation preventing strands extend along and are bounded to opposed circumferential portions of a number of the plurality of the openings.

3. The article according to claim 2, wherein 50% or more of the plurality of openings have circumferential portions along and to which the deformation preventing strands are bonded.

4. The article according to claim 1, wherein 50% or more of the plurality of openings have circumferential portions along and to which the deformation preventing strands are bonded.

5. The article according to claim 1, wherein said circumferential portions of the openings are defined by peripheral edges thereof at the level of said skin-contactable surface.

6. The article according to claim 1, wherein said circumferential portions of the openings are defined by inner peripheral walls thereof which extend between said skin-contactable and skin-noncontactable surfaces.

7. The article according to claim 1, wherein said circumferential portions of the openings are defined both by peripheral edges thereof at the level of said skin-contactable surface and by inner peripheral walls thereof which extend between said skin-contactable and skin-noncontactable surfaces.

8. The article according to claim 1, wherein the plurality of openings have a diameter of about 0.5 to about 3 mm and the deformation preventing strands have a diameter of about 0.1 to about 0.5 mm.

9. A body fluids absorbent article having a liquid-permeable topsheet, a liquid-impermeable backsheet and a liquid-absorbent core located between the liquid-permeable topsheet and the liquid-impermeable backsheet, wherein:

said liquid-permeable topsheet is formed from a nonwoven fabric made from thermoplastic synthetic fibers with a fineness of 0.05~8 deniers so as to have a basis weight of 10~50 g/m$^2$; said liquid-permeable topsheet is defined by a skin-contactable surface intended to come in contact with the wearer's skin and a skin-noncontactable surface intended not to come in contact with wearer's skin; a plurality of openings each having a diameter of 0.5~3 mm extend through said liquid-permeable topsheet from said skin-contactable surface to the skin-noncontactable surface, and queue up in parallel one to another so as to form a plural columns of said openings and, in one half or more of a total number of said openings, strands of thermoplastic synthetic resin each having a diameter of 0.1~0.5 mm extend along and are bonded to circumferential portions of the openings.

10. The article according to claim 9, herein said liquid-permeable topsheet includes tubular portions extending downward from the peripheral edges of the respective openings defined at the level of said skin-contactable surface and portion of said strands extend along and are bonded to circumferential parts of inner peripheral surfaces of the respective tubular portions.

11. The article according to claim 9, wherein said strands extend in parallel to said columns of openings and are bonded to said skin-contactable surface of said liquid-permeable topsheet between each pair of adjacent openings in each column of openings.

12. The article according to claim 9, wherein said strands and said nonwoven fabric are bonded together by means of heat-sealing.

13. The article according to claim 9, wherein said circumferential portions of the openings are defined by peripheral edges thereof at the level of said skin-contactable surface.

14. The article according to claim 9, wherein said circumferential portions of the openings are defined by inner peripheral walls thereof which extend between said skin-contactable and skin-noncontactable surfaces.

15. The article according to claim 9, wherein said circumferential portions of the openings are defined both by peripheral edges thereof at the level of said skin-contactable surface and by inner peripheral walls thereof which extend between said skin-contactable and skin-noncontactable surfaces.

* * * * *